(12) United States Patent
Szczepaniak et al.

(10) Patent No.: US 9,533,937 B2
(45) Date of Patent: Jan. 3, 2017

(54) USE OF METAL SCAVENGERS FOR REMOVAL OF RUTHENIUM RESIDUES

(71) Applicant: Apeiron Synthesis S.A., Wroclaw (PL)

(72) Inventors: Grzegorz Szczepaniak, Warsaw (PL); Stefan J. Czarnocki, Losice (PL); Krzysztof Skowerski, Jablonowo Pomorskie (PL)

(73) Assignee: Apeiron Synthesis S.A., Wroclaw (PL)

( * ) Notice: Subject to any disclaimer, the term of this patent is extended or adjusted under 35 U.S.C. 154(b) by 0 days.

(21) Appl. No.: 14/443,048

(22) PCT Filed: Jun. 24, 2014

(86) PCT No.: PCT/IB2014/062564
§ 371 (c)(1),
(2) Date: May 14, 2015

(87) PCT Pub. No.: WO2014/174501
PCT Pub. Date: Oct. 30, 2014

(65) Prior Publication Data
US 2016/0297742 A1 Oct. 13, 2016

(30) Foreign Application Priority Data

Dec. 31, 2013 (PL) ........................................ 406739

(51) Int. Cl.
| | | |
|---|---|---|
| C07C 67/56 | (2006.01) | |
| C22B 11/00 | (2006.01) | |
| C07C 67/48 | (2006.01) | |
| B01J 31/22 | (2006.01) | |
| C07C 291/00 | (2006.01) | |
| C22B 3/00 | (2006.01) | |
| C07C 291/10 | (2006.01) | |

(52) U.S. Cl.
CPC ............ *C07C 67/56* (2013.01); *B01J 31/2278* (2013.01); *C07C 67/48* (2013.01); *C22B 11/048* (2013.01); *B01J 2231/324* (2013.01); *B01J 2531/821* (2013.01); *C07C 291/10* (2013.01); *C07C 2101/10* (2013.01)

(58) Field of Classification Search
CPC ...... C07C 67/56; C07C 67/48; C07C 2101/10; C07C 291/10; C22B 11/048; B01J 31/2278; B01J 2231/324; B01J 2531/821
See application file for complete search history.

(56) References Cited

PUBLICATIONS

McEleney ("Functionalized Mesoporous Silicates for the Removal of Ruthenium from Reaction Mixtures" Organic Letters vol. 8, No. 13, 2006, p. 2663-2666).*
International Search report and written opinion for parent application PCT/IB2014/062564, p. 1-6, mailed on Jan. 29, 2015.*
French et al., "Removal of Ruthenium Using a Silica Gel Supported Reagent," *Organic Letters* 15(21):5416-5419, 2013.
Galan et al., "A Rapid and Simple Cleanup Procedure for Metathesis Reactions," *Organic Letters* 9(7):1203-1206, 2007.
Leon et al., "Multiple Multicomponent Macrocyclizations Including Bifunctional Building Blocks (MiBs) Based on Staudinger and Passerini Three-Component Reactions," *J. Org. Chem.* 73:1762-1767, 2008.
Magano et al., "Large-Scale Applications of Transition Metal-Catalyzed Couplings for the Synthesis of Pharmaceuticals," *Chem. Rev.* 111:2177-2250, 2011.
Rivera et al., "Supramolecular Compounds from Multiple Ugi Multicomponent Macrocyclizations: Peptoid-based Cryptands, Cages, and Cryptophanes," *J. Am. Chem. Soc.* 128:7122-7123, 2006.
Rivera et al., "Rapid generation of macrocycles with natural-product-like side chains by multiple multicomponent macrocyclizations (MiBs)," *Org. Biomol. Chem.* 6:1787-1795, 2008.
Smith et al., "Investigation of Some Dialkylamino Isocyanidesl," *J. Org. Chem.* 23(11):1599-1603, Nov. 1958.
Vougioukalakis, "Removing Ruthenium Residues from Olefin Metathesis Reaction Products," *Chem. Eur. J.* 18:8868-8880, 2012.

* cited by examiner

*Primary Examiner* — Jafar Parsa
*Assistant Examiner* — Amy C Bonaparte
(74) *Attorney, Agent, or Firm* — Seed IP Law Group LLP

(57) ABSTRACT

The invention concerns use of metal scavengers of the formula (1), wherein the variables are as defined in the description of the invention, for removal of ruthenium residues, compounds, or complexes thereof, from the post-reaction mixtures, from the products of reactions catalyzed with ruthenium complexes, as well as from organic compounds contaminated with ruthenium.

(1)

17 Claims, No Drawings

USE OF METAL SCAVENGERS FOR REMOVAL OF RUTHENIUM RESIDUES

FIELD OF THE INVENTION

The invention relates to use of metal scavengers, especially use of ruthenium scavengers, for removal of ruthenium residues from the post-reaction mixtures, from the products of reactions catalysed by complexes of ruthenium, and also from organic compounds contaminated with ruthenium.

THE BACKGROUND ART

Catalysts for many organic reactions of key scientific and industrial significance, such as metathesis of olefins, Mizoroku-Heck, Negishi, Sonogashira, and Suzuki coupling, Noyori asymmetric hydrogenation, or Sharpless asymmetric epoxidation, are in the form of transition metal complexes. One of the greatest problems related to the use of compounds of such type in the synthesis, consists in removal of the metal residues from the products of reactions. This issue is particularly important for the pharmaceutical industry because of restrictive standards related to acceptable heavy metal contents in the biologically active compounds, being below 10 ppm (see, European Medicines Agency, *Specification limits for residues of metal catalysts CHMP/SWP/4446/2000*, 2008). Many examples of pharmaceutical syntheses demonstrate that this problem is very common and troublesome (see, J. Magano, J. R. Dunetz *Chem. Rev.* 2011, 111, 2177-2250). This problem may be solved in the following ways:
1. by the means of "classic" purification techniques such as crystallisation, extraction, chromatography;
2. by using of specially designed catalysts that are easily removable after the completed reaction, so called self-scavenging catalysts;
3. by adding transition metal scavengers, i.e., the compounds that bind metals and are easily removable after binding metals, to the post-reaction mixtures or reaction products.

The "classic" purification techniques not always make it possible to obtain a pure product with low metal contents, below 10 ppm. On the other hand, self-scavenging catalysts are either hardly available or expensive. The advantage of metal scavengers resides in their universality. The same scavenger compound can often be used in combination with many types of catalysts of various reactions, thanks to this fact such an approach is more general. An ideal metal scavenger should feature the following properties:
1. to bind various forms of transition metal complexes, at various oxidation states, quickly, irreversibly and quantitatively;
2. to be efficient at slight excess with respect to the catalyst used;
3. to be easily removable in the form bound to the transition metal, by extraction, crystallisation, or chromatography;
4. to be inexpensive and easily obtainable;
5. to be stable in the air and against the moisture, non-toxic, safe, odourless, and conveniently applicable;
6. to be either insoluble or very soluble in typical organic solvents.

Ruthenium scavengers are well-known in the state of the art (see, Table 1 for examples). Some of them are commercially available, but only few of them possess most of the above-mentioned features (see, G. C. Vougioukalakis, *Chem. Eur. J.* 2012, 18, 8868-8880). Their most important drawbacks comprise the need to use a large excess of the scavenger with respect to the (pre)catalyst (50-500 equivalents), prolonged time required to bind the scavengers to the transition metals (12 hours), high level of contamination of the product with ruthenium after purification (above 10 ppm, see the last column of Table 1), poor solubility in typical, low-polar organic solvents (i.e., diethyl ether, tetrahydrofuran, toluene, dichloromethane), moderate stability in the air, high price.

TABLE 1

[Reaction scheme: diethyl diallylmalonate → cyclopentene product via 1. Grubbs 1st 5 mol %, 2. metal scavenger, 3. purification]

| Entry | metal scavenger | mol % | time [hours] | purification method | Ru contamination of the product [ppm] |
|---|---|---|---|---|---|
| 1[a] | HO-P(CH₂CH₂OH)₃ type (tris(hydroxymethyl)phosphine-like) | 430 | 0.16 | extraction | 670 |
| 2[a] | | 430 | 0.16 | adding SiO₂, filtration | 206 |
| 3[b] | DMSO (H₃C-S(=O)-CH₃) | 250 | 12 | chromatography over SiO₂ | 360 |
| 4[b] | triphenylphosphine oxide (Ph₃P=O) | 250 | 12 | chromatography over SiO₂ | 240 |

TABLE 1-continued

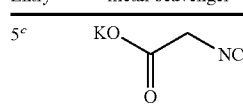

| Entry | metal scavenger | mol % | time [hours] | purification method | Ru contamination of the product [ppm] |
|---|---|---|---|---|---|
| 5[c] | 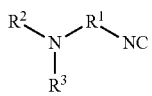 | 44 | 12 | chromatography over $SiO_2$ | 220 |

[a]see, R.H. Grubbs, Tetrahedron Lett., 1999, 40, 4137-4140, [b]see, G.I. Georg, Org. Lett., 2001, 3, 1411-1413, [c]see, S.T. Diver, Org. Lett., 207, 9, 1203-1206.

DISCLOSURE OF THE INVENTION

It was found that the metal scavengers, especially ruthenium scavengers, represented by the formula (1):

$$\underset{R^3}{\overset{R^2}{\diagdown}}\underset{|}{N}\overset{R^1}{\diagup}NC \qquad 1$$

having at least one isonitrile (—NC) group and at least one tertiary nitrogen atom in their structure demonstrate much higher efficiency in removing ruthenium residues from the post-reaction mixtures compared to the metal scavengers known from the state of the art. Moreover, it was unexpectedly found that the metal scavengers represented by the formula (1), in the presence of ruthenium compounds, complexes, or residues, form compounds very easily binding silica gel, making it possible to remove them easily and quantitatively by chromatography or filtration. It was also unexpectedly found that the metal scavengers represented by the formula (1), containing the piperazine ring in their structure, possess a good solubility in solvents having a broad spectrum of polarity. This is of very high practical significance. Moreover, the compounds of the formula (1) are very stable both in the solid state as well as in the solution, and also they are devoid of a very unpleasant odour typical for organic isonitriles. Their synthesis may be carried out efficiently in two steps from the readily available substrates of the formula $R^2N(R^3)R^1NH_2$.

DETAILED DESCRIPTION OF THE INVENTION

The invention concerns use of metal scavengers of the formula (1), that contain at least one isonitrile (—NC) group and at least one tertiary nitrogen atom in their structure, for removal of ruthenium residues, compounds, or complexes thereof, from the post-reaction mixtures, from the products of reactions catalysed with ruthenium complexes as well as from organic compounds contaminated with ruthenium, where in the formula (1):

$$\underset{R^3}{\overset{R^2}{\diagdown}}\underset{|}{N}\overset{R^1}{\diagup}NC \qquad 1$$

$R^1$ represents $C_2$-$C_{25}$ alkyl, $C_2$-$C_{25}$ alkenyl, $C_2$-$C_{25}$ alkynyl, $C_3$-$C_7$ cycloalkyl, $C_3$-$C_{25}$ cycloalkenyl, $C_8$-$C_{25}$ cycloalkynyl, $C_5$-$C_{24}$ aryl, $C_5$-$C_{20}$ heteroaryl or $C_3$-$C_{12}$ heterocyclyl, being substituted with at least one isonitrile (—NC) group; $R^2$ and $R^3$ represent, independently from each other, $C_2$-$C_{25}$ alkyl, $C_2$-$C_{25}$ alkylalkoxy, $C_1$-$C_{25}$ alkylamino, $C_2$-$C_{25}$ alkoxy, $C_2$-$C_{25}$ alkenyl, $C_3$-$C_7$ cycloalkyl, $C_3$-$C_{25}$ cycloalkenyl, $C_2$-$C_{25}$ alkynyl, $C_8$-$C_{25}$ cycloalkynyl, $C_5$-$C_{24}$ aryl, $C_5$-$C_{20}$ heteroaryl or $C_3$-$C_{12}$ heterocyclyl, being unsubstituted or substituted with at least one isonitrile (—NC) group, wherein $R^2$ and $R^3$ may be bound together to form a heterocyclic $C_4$-$C_{16}$ system, being unsubstituted or substituted with at least one or more isonitrile (—NC) or (—R'NC) group, wherein R' represents $C_1$-$C_{12}$ alkyl, $C_5$-$C_{24}$ aryl, $C_5$-$C_{20}$ heteroaryl or $C_3$-$C_{12}$ heterocyclyl.

In the preferred embodiment,
$R^1$ represents $C_2$-$C_{25}$ alkyl, $C_2$-$C_{25}$ alkenyl, $C_2$-$C_{25}$ alkynyl, $C_3$-$C_7$ cycloalkyl, $C_3$-$C_{25}$ cycloalkenyl, $C_8$-$C_{25}$ cycloalkynyl, $C_5$-$C_{24}$ aryl, $C_5$-$C_{20}$ heteroaryl or $C_3$-$C_{12}$ heterocyclyl;
$R^2$ and $R^3$ represent, independently from each other, $C_2$-$C_{25}$ alkyl, $C_2$-$C_{25}$ alkylalkoxy, $C_1$-$C_{25}$ alkylamino, $C_2$-$C_{25}$ alkoxy, $C_2$-$C_{25}$ alkenyl, $C_3$-$C_7$ cycloalkyl, $C_3$-$C_{25}$ cycloalkenyl, $C_2$-$C_{25}$ alkynyl, $C_8$-$C_{25}$ cycloalkynyl, $C_5$-$C_{24}$ aryl, $C_5$-$C_{20}$ heteroaryl or $C_3$-$C_{12}$ heterocyclyl, being unsubstituted or substituted with at least one isonitrile (—NC) group, wherein $R^2$ and $R^3$ may be bound together to form a heterocyclic $C_4$-$C_{16}$ system, being unsubstituted or substituted with isonitrile (—NC) group or (—R'NC) group, wherein R' represents $C_1$-$C_{12}$ alkyl.

In the more preferred embodiment:
$R^1$ represents $C_2$-$C_{25}$ alkyl, $C_2$-$C_{25}$ alkenyl, $C_2$-$C_{25}$ alkynyl, $C_3$-$C_7$ cycloalkyl, $C_3$-$C_{25}$ cycloalkenyl, $C_8$-$C_{25}$ cycloalkynyl, $C_5$-$C_{24}$ aryl, $C_5$-$C_{20}$ heteroaryl or $C_3$-$C_{12}$ heterocyclyl;
$R^2$ and $R^3$ represent, independently from each other, $C_2$-$C_{25}$ alkyl, $C_2$-$C_{25}$ alkylalkoxy, $C_1$-$C_{25}$ alkylamino, $C_2$-$C_{25}$ alkoxy, $C_2$-$C_{25}$ alkenyl, $C_3$-$C_7$ cycloalkyl, $C_3$-$C_{25}$ cycloalkenyl, $C_2$-$C_{25}$ alkynyl, $C_8$-$C_{25}$ cycloalkynyl, $C_5$-$C_{24}$ aryl, $C_5$-$C_{20}$ heteroaryl or $C_3$-$C_{12}$ heterocyclyl, being unsubstituted or substituted with at least one isonitrile (—NC) group, wherein $R^2$ and $R^3$ may be bound together to form the ring system selected from nitrogen heterocycles such as aziridine, azetidine, diazetidine, pyrrolidine, imidazolidine, oxazolidine, thiazolidine, piperidine, piperazine, morpholine, azepane, 1,5,7-triaza-bicyclo[4.4.0]dec-5-ene, being unsubstituted or substituted with isonitrile (—NC) group or (—R'NC) group, wherein R' represents $C_1$-$C_{12}$ alkyl.

Preferably, $R^1$ represents $C_2$-$C_{25}$ alkyl, $C_3$-$C_7$ cycloalkyl, $C_5$-$C_{24}$ aryl, $C_5$-$C_{20}$ heteroaryl or $C_3$-$C_{12}$ heterocyclyl;
$R^2$ and $R^3$ represent, independently from each other, $C_2$-$C_{25}$ alkyl, $C_2$-$C_{25}$ alkylalkoxy, $C_1$-$C_{25}$ alkylamino, $C_2$-$C_{25}$ alkoxy, $C_2$-$C_{25}$ alkenyl, $C_3$-$C_7$ cycloalkyl, $C_3$-$C_{25}$ cycloalkenyl, $C_2$-$C_{25}$ alkynyl, $C_8$-$C_{25}$ cycloalkynyl, $C_5$-$C_{24}$ aryl, $C_5$-$C_{20}$ heteroaryl or $C_3$-$C_{12}$ heterocyclyl, being unsubstituted or substituted with at least one isonitrile (—NC) group, wherein $R^2$ and $R^3$ may be bound together to form the ring system selected from nitrogen heterocycles such as pyrrolidine, imidazolidine, oxazolidine, piperidine, piperazine, morpholine, azepane, 1,5,7-triaza-bicyclo[4.4.0]dec-5-ene, being unsubstituted or substituted with isonitrile (—NC) group or (—R'NC) group, wherein R' represents $C_1$-$C_{12}$ alkyl.

Preferably, the metal scavengers of the structural formula (1) is used for removing residues of the ruthenium compounds or complexes from the olefin-metathesis post-reaction mixtures, from the olefin-metathesis reaction products, as well as from the organic compounds which were synthesized using olefin metathesis.

Preferably, the metal scavenger selected from the following formulae (2), (3), (4) and (5):

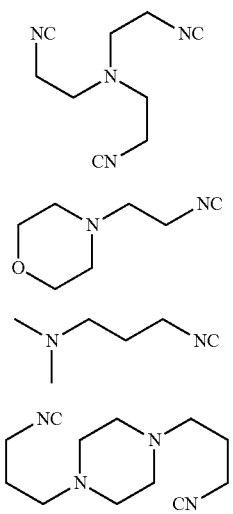

is used for removing residues of the ruthenium compounds or complexes from the olefin-metathesis post-reaction mixtures, from the olefin-metathesis reaction products, as well as from the organic compounds which were synthesized using olefin metathesis.

The invention concerns also use of two or more metal scavengers, as defined by the above formula (1), for removing residues of the ruthenium compounds or complexes from the olefin-metathesis post-reaction mixtures, from the olefin-metathesis reaction products, as well as from the organic compounds which were synthesized using olefin metathesis.

Preferably, the metal scavenger of the formula (1) is added to the post-reaction mixture or to the contaminated organic compound dissolved in an organic solvent; alternatively, a solution of the metal scavenger of the formula (1) in an organic solvent or water is prepared, and this is added to the post-reaction mixture or to the contaminated organic compound dissolved in an organic solvent.

Preferably, the time of purification of the post-reaction mixtures or the solutions of organic compounds contaminated with the residues of ruthenium compounds or complexes by the metal scavenger of the formula (1) is in the range from 1 minute to 48 hours.

Preferably, the process of purification using the metal scavenger of the formula (1) is carried out at a temperature ranging from 0 to 120° C.

Preferably, after adding the metal scavenger of the formula (1), the post-reaction mixture or the organic compound solution is filtered through a silica gel. Preferably, filtration is carried out using from 20 to 10000 weight % of the silica gel with relation to the (pre)catalyst used.

Preferably, the silica gel (from 20 to 10000 weight % with relation to the (pre)catalyst used) is added to the post-reaction mixture or the organic compound solution containing the metal scavenger of the formula (1), the whole mixture is stirred for a period of from 1 minute to 48 hours, followed by filtering off the contaminated silica gel.

The particularly preferred metal scavenger is the novel compound of the formula (5),

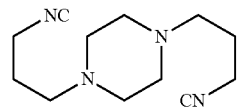

that constitutes the separate aspect of this invention.

The terms "alkyl group" and "alkyl" denote a saturated, linear, or branched hydrocarbyl substituent having the indicated number of carbon atoms. The examples of a linear alkyl substituent are methyl, ethyl, n-propyl, n-butyl, n-pentyl, n-hexyl, n-heptyl, n-octyl, n-nonyl, and n-decyl. The representative branched $C_3$-$C_{10}$ alkyl substituents comprise isopropyl, sec-butyl, isobutyl, tert-butyl, isopentyl, neopentyl, 1-methylbutyl, 2-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, 3,3-dimethylheptyl, and the like.

The term "alkoxy group" or "alkoxy" refers to the alkyl substituent as defined above, linked by an oxygen atom.

The term "group alkylalkoxy" or "alkylalkoxy" refers to the alkyl group as defined above, substituted with an alkoxy substituent as defined above.

The term "alkylamino group" refers to the alkyl substituent as defined above, linked by a nitrogen atom, wherein the free valence of the nitrogen atom is saturated with a hydrogen atom.

The term "alkenyl group" or "alkenyl" refers to the linear or branched acyclic hydrocarbyl substituent having the indicated number of carbon atoms and containing at least one carbon-carbon double bond. The representative alkenyl substituents comprise vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl, and the like.

The term "alkynyl group" or "alkynyl" refers to a saturated, linear, or branched acyclic hydrocarbyl substituent having the indicated number of carbon atoms and containing at least one carbon-carbon triple bond. The representative alkynyl substituents comprise acetylenyl (ethynyl), propynyl, 1-butynyl, 2-butynyl, 1-pentynyl, 2-pentynyl, 3-methyl-1-butynyl, 4-pentynyl, 1-hexynyl, 2-hexynyl, 5-hexynyl, and the like.

The term "cycloalkyl group" or "cycloalkyl" refers to a saturated mono- or polycyclic hydrocarbyl substituent having the indicated number of carbon atoms. The representative cycloalkyl substituents comprise cyclopropyl, cyclobutyl, cyclopentyl, cyclohexyl, cycloheptyl, cyclooctyl, cyclononyl, cyclodecyl, and the like.

The term "cycloalkenyl group" or "cycloalkenyl" refers to a saturated mono- or polycyclic hydrocarbyl substituent having the indicated number of carbon atoms and containing at least one carbon-carbon double bond. The examples of the cycloalkenyl substituents comprise cyclopentenyl, cyclopenta-dienyl, cyclohexenyl, cyclohexadienyl, cycloheptenyl, cyclo-heptadienyl, cycloheptatrienyl, cyclooctenyl, cycloocta-dienyl, cyclooctatrienyl, cyclooctatetraenyl, cyclononenyl, cyclononadienyl, cyclodecenyl, cyclodekadienyl, and the like.

The term "cycloalkynyl group" or "cycloalkynyl" refers to a saturated mono- or polycyclic hydrocarbyl substituent having the indicated number of carbon atoms and contain at least one carbon-carbon triple bond. The examples of the cycloalkynyl substituents comprise cyclooctynyl, cyclononynyl, cyclo-decynyl, and the like.

The term "aryl group" or "aryl" refers to an aromatic, mono- or polycyclic, hydrocarbyl substituent having the indicated number of carbon atoms. The examples of aryl substituents comprise phenyl, tolyl, xylyl, naphthyl, and the like.

The term "heteroaryl" refers to an aromatic mono- or polycyclic hydrocarbyl substituent having the indicated number of carbon atoms, wherein at least one carbon atom has been substituted with a heteroatom selected from O, N and S. The examples of heteroaryl substituents comprise furyl, thienyl, imidazolyl, oxazolyl, triazolyl, isoxazolyl, triazolyl, oxadiazolyl, thiadiazolyl, tetrazolyl, pyridyl, pyrimidyl, triazinyl, indolyl, benzo[b]furyl, benzo[b]thienyl, indazolyl, benzimidazolyl, azaindolyl, quinolyl, isoquinolyl, carbazolyl, and the like.

The term "heterocyclic group" refers to a saturated or partially unsaturated, mono- or polycyclic hydrocarbyl substituent, having the indicated number of carbon atoms, wherein at least one carbon atom has been substituted with a heteroatom selected from O, N and S. The examples of heterocyclic substituents comprise furyl, thiophenyl, pyrrolyl, oxazolyl, imidazolyl, thiazolyl, isoxazolyl, pyrazolyl, iso-thiazolyl, triazinyl, pyrrolidinonyl, pyrrolidinyl, hydantoinyl, oxiranyl, oxetanyl, tetrahydrofuranyl, tetrahydrothiophenyl, quinolinyl, isoquinolinyl, chromonyl, coumarinyl, indolyl, indolizinyl, benzo[b]furanyl, benzo[b]thiophenyl, indazolyl, purinyl, 4H-quinolizinyl, isoquinolyl, quinolyl, phthalazinyl, naphthyridinyl, carbazolyl, β-carbolinyl, and the like.

Now the invention will be illustrated with the following examples that are intended to help better understanding the invention, and in no way to limit its scope.

The commercially available compounds (Sigma-Aldrich, Strem Chemicals, Alfa Aesar) were used for the reactions without any further purification. The compounds (3) and $CNCH_2CO_2K$ were obtained from Sigma-Aldrich. The reactions performed in the protective argon atmosphere have been carried out by the Schlenk technique using pre-dried vessels, using dry, deoxygenated solvents, distilled in the protective argon atmosphere from the drying agents; toluene was distilled over potassium; dichloromethane was distilled over $CaH_2$. The reactions performed without using any protective argon atmosphere, in the air, were carried out using dichloromethane and toluene of HPLC grade (Sigma-Aldrich). The reaction course was monitored using thin-layer chromatography (TLC), with plates coated with silica gel and the fluorescent indicator (Merck Kieselgel 60 F254). The TLC plates were visualised in the UV light at 254 nm or by developing in an aqueous solution of $KMnO_4$. The gravitational or flash separations by a chromatographic column were carried out using the silica gel (Merck Silica Gel 60, 230-400 mesh). The silica gel filtrations were carried out using the silica gel (Merck Silica Gel 60, 230-400 mesh). The NMR spectra were recorded using a Bruker Avance 300 MHz spectrometer. The chemical shifts are reported in ppm relative to TMS (δ=0 ppm) as an internal standard or relative to chloroform-$d_1$ (δ=7.26 ppm). The post-reaction mixtures were analysed by gas chromatography (GC) using a Clarus® 580 GC apparatus from PerkinElmer, with an InterCap 5MS/Sil column having the length of 30 m and the diameter of 0.25 mm.

Example I

Synthesis of the Metal Scavenger (Formula 2)

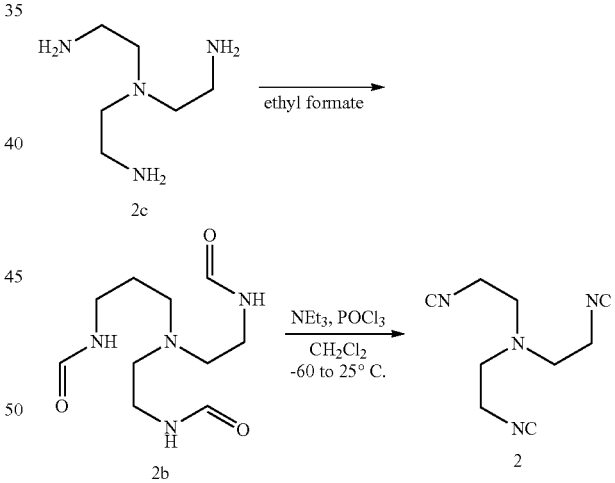

The compound (2) was obtained according to the literature procedure (see, D. G. Rivera, L. A. Wessjohann, *J. Am. Chem. Soc.* 2006, 128, 7122).

5 ml (50 mmol) of tri(2-aminoethyl)amine were added to 100 ml of ethyl formate. The reaction mixture was heated at a boiling temperature for 20 hours. The solvents were evaporated in vacuo, affording quantitatively the product (2b) as a yellow oil. The compound (2b) was used in the next step without any further purification. Using the protective argon atmosphere, the Schlenk vessel was charged with the triformamide (2b), to which was added 60 ml of dry triethylamine and 60 ml of dry dichloromethane. The suspension contained in the Schlenk vessel was cooled down to −60° C.

Then the mixture of POCl$_3$ (13.8 ml, 150 mmol) in dry dichloromethane (40 ml) was slowly added (over 30 minutes). The reaction was stirred at room temperature for 16 hours. Since that moment all further operations were carried out without using any protective argon atmosphere. The reaction mixture was poured into ice-cooled water (200 ml). The crude product was extracted with dichloromethane (2×100 ml). The organic phases were combined, then washed with a saturated aqueous solution of NaHCO$_3$ and dried over anhydrous Na$_2$SO$_4$. The solvents were evaporated in vacuo. The crude product (2) was chromatographed over a silica gel, using 1% of triethylamine in dichloromethane as an eluent, to afford the compound (2) in 69% yield (5.83 g) as a light yellow oil. The $^1$H NMR and $^{13}$C spectra were consistent with the literature data.

Example II

The Synthesis of the Metal Scavenger (Formula 4)

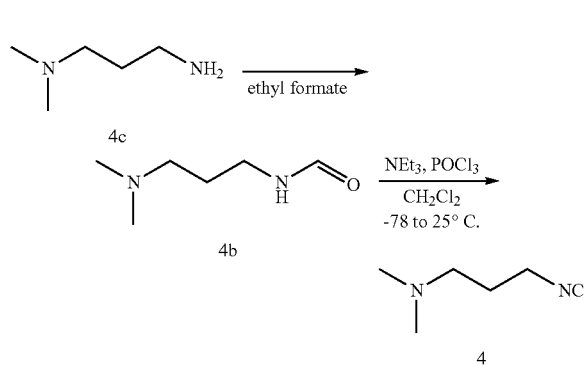

5 ml (50 mmol) of N,N-dimethyl-1,3-propanediamine were added to 20 ml of ethyl formate. The flask contents were stirred for 24 hours. The solvents were evaporated in vacuo, affording quantitatively the product (4b) as a colourless oil. The compound (4b) was used in the next step without any further purification. Using the protective argon atmosphere, the Schlenk vessel was charged with the formamide (4b), to which 20 ml of dry triethylamine and 60 ml of dry dichloromethane were added. The suspension contained in the Schlenk vessel was cooled down to −78° C. using a cooling bath (acetone/dry ice). Then 7.5 ml (2 equivalents) POCl$_3$ were slowly added. The cooling bath was removed after 15 minutes. The reaction was stirred at room temperature for 2 hours. Since that moment all further operations were carried out without using any protective argon atmosphere. The reaction mixture was poured into an ice-cooled aqueous solution of K$_2$CO$_3$ (100 ml, 1.0 g/ml). The obtained solution was vigorously stirred for 30 minutes. Then 100 ml of dichloromethane were added, and extraction was carried out. The aqueous phase was washed with dichloromethane (50 ml). The organic phases were combined and dried with anhydrous MgSO$_4$. The solvents were evaporated in vacuo. The crude product (4) was chromatographed over a silica gel, using 1% of triethylamine in dichloromethane as an eluent, to afford the compound (4) in 48% yield (2.1 g) as a colourless oil. The physicochemical data were consistent with the literature data (P. A. S. Smith, N. W. Kalanda, J. Org. Chem., 1958, 1599-1603).

Example III

The Synthesis of the Metal Scavenger (Formula 5)

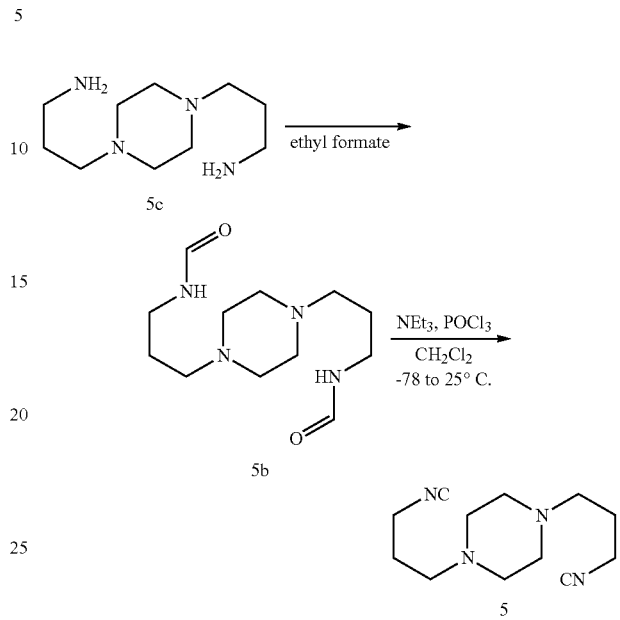

10 ml (47.6 mmol) of 1,4-di(3-aminopropyl)piperazine were slowly added to 30 ml (8 equivalents) of ethyl formate. The flask contents were vigorously stirred for 1 hour. As the reaction proceeded, the product precipitated from the reaction mixture. 50 ml of ethyl acetate were added, the whole mixture was stirred for 30 minutes. The precipitated product was filtered off using a Buchner funnel, washed with ethyl acetate and dried in vacuo, to afford the compound (5b) quantitatively as a white solid. The compound (5b) was used in the next step without any further purification. Using the protective argon atmosphere, the Schlenk vessel was charged with 1.76 g (6.87 mmol) of the compound 5b, to which 8.4 ml of dry triethylamine and 30 ml of dry dichloromethane were added. The suspension contained in the Schlenk vessel was cooled down to −78° C. using a cooling bath (acetone/dry ice). Then 3.16 ml (3 equivalents) of POCl$_3$ were slowly added. The cooling bath was removed after 15 minutes. The reaction was stirred at room temperature for 2 hours. Since that moment all further operations were carried out without using any protective argon atmosphere. The reaction mixture was poured into the ice-cooled aqueous solution of K$_2$CO$_3$ (50 ml, 1.42 g/ml). The obtained solution was vigorously stirred for 30 min. Then 70 ml of dichloromethane were added and extraction was carried out. The aqueous phase was washed with dichloromethane (50 ml). The organic phases were combined and dried with anhydrous MgSO$_4$. The solvents were evaporated in vacuo. 1 ml of triethylamine, 5 ml of dichloromethane and 2.0 g of the silica gel were added to the crude product. The solvents were evaporated in vacuo. The whole residue was put onto a column containing silica gel (5.0 g). Chromatography was carried out using 2% of triethylamine in dichloromethane (50 ml) as an eluent. The solvents were evaporated in vacuo, then the product was crystallised from cyclohexane (50 ml), to afford the compound (5) as white crystals in 79% yield (1.19 g).

$^1$H NMR (300 MHz, CDCl$_3$) δ 3.53-3.37 (m, 4H), 2.55-2.35 (m, 12H), 1.91-1.72 (m, 4H). $^{13}$C NMR (75 MHz, CDCl$_3$) δ 156.0 (t), 54.5, 53.2, 39.6 (t), 26.6.

Example IV

General Procedure for Removal of Ruthenium Residues from the Post-Reaction Mixtures with the Metal Scavengers Using Filtration Through Silica Gel Using the protective argon atmosphere, the Schlenk vessel was charged with 1.25 mmol of diethyl diallylmalonate or [1-(allyloxy)prop-2-yne-1,1-diyl]dibenzene, respectively, and a dry, deoxygenated solvent (25 ml; CH$_2$Cl$_2$ or toluene, respectively). The reaction mixture was warmed to the predetermined temperature, then 0.0125 mmol (1.0 mol %) of the (pre)catalyst was added. The obtained solution was stirred at the predetermined temperature for 1 hour. Since that moment all further operations were carried out without using any protective argon atmosphere. The reaction mixture was cooled to room temperature, an appropriate amount of the metal scavenger (0.00438 mmol (0.35 mol %)-0.11 mmol (8.8 mol %) was added in 1 ml of the reaction solvent; or, in the case of the scavenger CNCH$_2$CO$_2$K, in 1 ml of methanol. The obtained solution was stirred at room temperature for 30 minutes. The reaction mixture was gravitationally filtered through a short column filled with silica gel (200 weight % of SiO$_2$ with relation to the (pre)catalyst used, 1.6 cm column diameter). Then an additional portion of the reaction solvent (20 ml) was driven through the column. The solvents were concentrated in vacuo, to yield the product as an oil. The reaction conversion was determined by gas chromatography. The content of ruthenium in the product was determined by ICP-MS measurements. The results of tests for removing ruthenium residues are presented in Tables 2-4. The last column of the Table presents the level of contamination of the product with ruthenium after purification.

TABLE 2

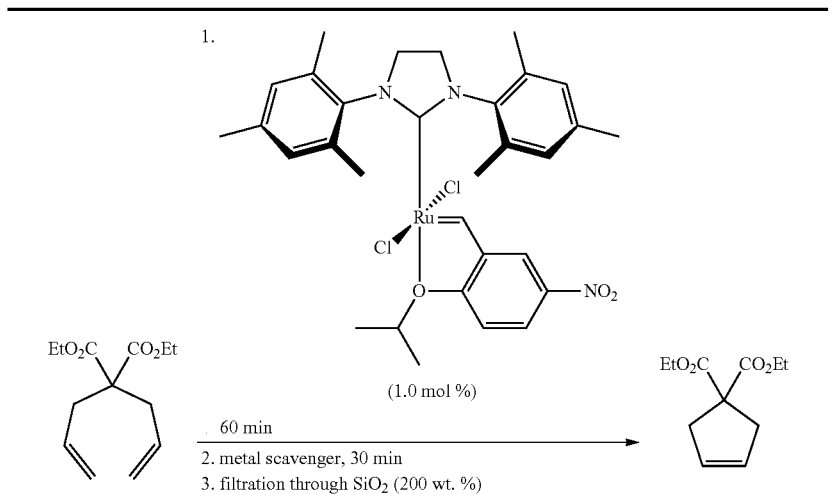

| Entry | metal scavenger | mol % | temp [° C.] | solvent | reaction conversion [%] | Ru contamination of the product [ppm] |
|---|---|---|---|---|---|---|
| 1 | none | 4.4 | 22 | CH$_2$Cl$_2$ | 99 | 334 |
| 2 |  | 4.4 | 22 | CH$_2$Cl$_2$ | 99 | 17 |
| 3 |  | 8.8 | 22 | CH$_2$Cl$_2$ | 96 | 11 |
| 4 |  | 1.1 | 22 | CH$_2$Cl$_2$ | 99 | 22 |
| 5 |  | 2.2 | 22 | CH$_2$Cl$_2$ | 97 | 18 |
| 6 |  | 2.2 | 70 | toluene | 99 | 11 |
| 7 |  | 4.4 | 22 | CH$_2$Cl$_2$ | 96 | 1.6 |
| 8 |  | 4.4 | 70 | toluene | 96 | <0.0015 |
| 9 |  | 4.4 | 22 | toluene | 98 | <0.0015 |
| 10 |  | 0.35 | 22 | CH$_2$Cl$_2$ | 98 | 143 |
| 11 |  | 0.7 | 22 | CH$_2$Cl$_2$ | 99 | <0.0015 |
| 12 |  | 1.5 | 22 | CH$_2$Cl$_2$ | 99 | 6.4 |
| 13 |  | 2.9 | 22 | CH$_2$Cl$_2$ | 99 | 7.1 |
| 14 |  | 0.7 | 70 | toluene | 94 | <0.0015 |

TABLE 2-continued

Reaction: Diethyl diallylmalonate → diethyl cyclopent-3-ene-1,1-dicarboxylate using Ru catalyst (1.0 mol %) with N,N'-bis(2,4,6-trimethylphenyl)imidazolidine ligand and 2-isopropoxy-5-nitrobenzylidene, 60 min; 2. metal scavenger, 30 min; 3. filtration through SiO$_2$ (200 wt. %).

| Entry | metal scavenger | mol % | temp [° C.] | solvent | reaction conversion [%] | Ru contamination of the product [ppm] |
|---|---|---|---|---|---|---|
| 15 | KOOC-CH$_2$-NC | 2.2 | 22 | CH$_2$Cl$_2$ | 99 | 299 |
| 16 | | 4.4 | 22 | CH$_2$Cl$_2$ | 99 | 138 |
| 17 | | 8.8 | 22 | CH$_2$Cl$_2$ | 99 | 91 |
| 18 | | 8.8 | 70 | toluene | 99 | 247 |

TABLE 3

Reaction: Diethyl diallylmalonate → diethyl cyclopent-3-ene-1,1-dicarboxylate. 1. pre(catalyst), 1.0 mol %, 60 min, toluene, 70° C.; 2. metal scavenger, 30 min; 3. filtration through SiO$_2$.

| Entry | (pre)catalyst | metal scavenger (mol %) | reaction conversion [%] | Ru contamination of the product [ppm] |
|---|---|---|---|---|
| 1 | Hoveyda-Grubbs type (with isopropoxybenzylidene) | 5 (4.4) | 98 | 2.4 |
| 2 | | 3 (0.7) | 98 | <0.0015 |
| 3 | | CNCH$_2$CO$_2$K (8.8) | 96 | 142 |
| 4 | Grubbs 2nd gen. (with PCy$_3$ and benzylidene) | 5 (4.4) | 99 | 1.2 |
| 5 | | 3 (0.7) | 99 | 1.2 |
| 6 | | CNCH$_2$CO$_2$K (8.8) | 98 | 251 |

TABLE 3-continued
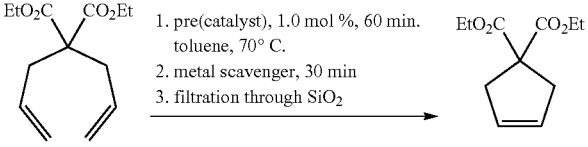
| Entry | (pre)catalyst | metal scavenger (mol %) | reaction conversion [%] | Ru contamination of the product [ppm] |
|---|---|---|---|---|
| 7 |  | 5 (4.4) | 94 | 14 |
| 8 |  | 3 (0.7) | 98 | 23 |
| 9 | 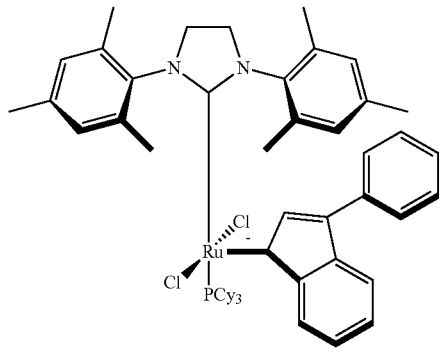 | CNCH$_2$CO$_2$K (8.8) | 99 | 159 |
| 10 |  | 5 (4.4) | 93 | 14 |
| 11 |  | 3 (4.4) | 95 | 16 |
| 12 | 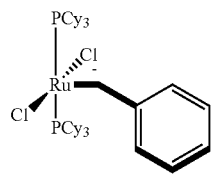 | CNCH$_2$CO$_2$K (8.8) | 92 | 370 |
TABLE 4
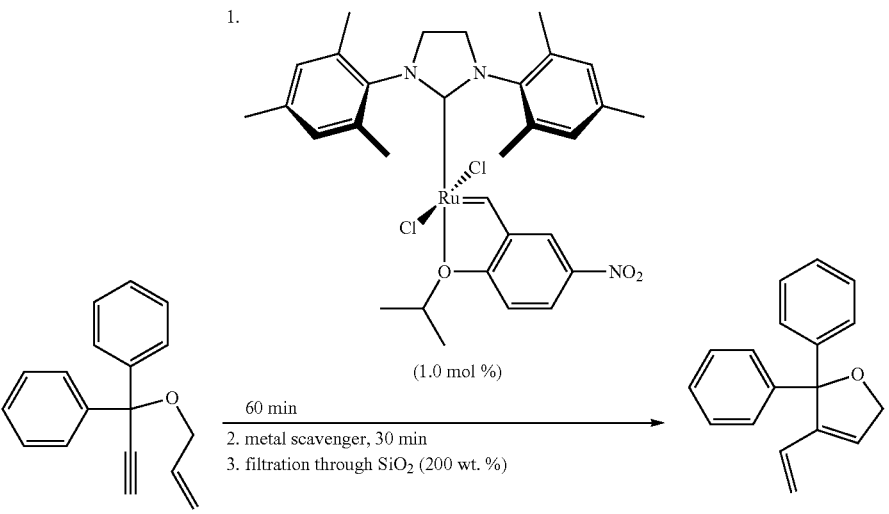
| Entry | metal scavenger | % mol | temp [° C.] | solvent | reaction conversion [%] | Ru contamination of the product [ppm] |
|---|---|---|---|---|---|---|
| 1 | 5 | 4.4 | 70 | toluene | 99 | 1.9 |
| 2 | 3 | 0.7 | 70 | toluene | 99 | <0.0015 |
| 3 | CNCH$_2$CO$_2$K | 8.8 | 70 | toluene | 99 | 189 |

Example V

General Procedure for Removal of Ruthenium Residues from the Post-Reaction Mixtures with the Metal Scavenger (5) with Addition of Silica Gel Using Filtration Using the protective argon atmosphere, the Schlenk vessel was charged with 300 mg (1.25 mmol) of diethyl diallylmalonate, and a dry, deoxygenated solvent (25 ml; $CH_2Cl_2$ or toluene). The reaction mixture was warmed to the predetermined temperature (as indicated in Table 5), then 0.0125 mmol (1.0 mol %) of the (pre)catalyst was added. The obtained solution was stirred at the predetermined temperature for 1 hour. Since that moment all further operations were carried out without using any protective argon atmosphere. The reaction mixture was cooled to room temperature, 0.55 mmol (4.4 mol %) of the metal scavenger (5) was added in 1 ml of the reaction solvent. The obtained solution was stirred at room temperature for 30 minutes. Then 200 weight % $SiO_2$ with relation to the (pre)catalyst used was added to the reaction mixture. The obtained suspension was stirred for 30 minutes. The silica gel was filtered off using cotton wool. The solvents were concentrated in vacuo, to yield the product as an oil. The reaction conversion was determined by gas chromatography. The content of ruthenium in the product was determined by ICP-MS measurements. The results of tests for removing ruthenium residues are presented in Table 5. The last column Table 5 reports the level of contamination of the product with ruthenium after purification.

TABLE 5

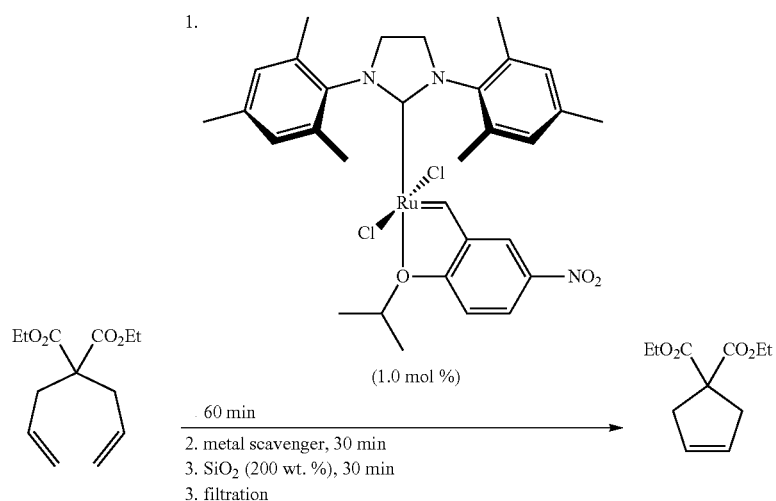

| Entry | metal scavenger | mol % | temp [° C.] | solvent | reaction conversion [%] | Ru contamination of the product [ppm] |
|---|---|---|---|---|---|---|
| 1 | 5 | 4.4 | 22 | $CH_2Cl_2$ | 99 | 11 |
| 2 | 5 | 4.4 | 22 | toluene | 99 | 6.6 |
| 3 | 5 | 4.4 | 70 | toluene | 99 | 0.85 |

SUMMARY OF THE INVENTION

These examples demonstrate that the metal scavengers according to the invention may be successfully used for removing residues of the ruthenium compounds or complexes from the olefin-metathesis post-reaction mixtures, from the olefin-metathesis reaction products, as well as from the organic compounds which were synthesized using olefin metathesis. Basing on the above-presented embodiment examples one may ascertain that, compared to the metal scavengers known from the state of the art, the compounds of the formula (1) according to the invention, used at a moderate excess with relation to the (pre)catalyst used (0.7-8.8 equivalents) and in a short period of time (30 minut), show a significantly superior efficiency in removing of ruthenium residues from the post-reaction mixtures. The isonitrile-containing scavenger $CNCH_2CO_2K$, known from the state of the art, provides much worse results in removing ruthenium. The products purified with the scavenger $CNCH_2CO_2K$ are contaminated with ruthenium at a level higher by one or two orders of magnitude than the products purified with the scavengers according to the invention. The compounds of the formula (1) according to the invention are very stable both in the solid state and in the solution, and also they are devoid of a very unpleasant odour typical for organic isonitriles, what makes them easy to use. Besides, the metal scavengers according to the invention, containing a piperazine ring in their structure, have good solubility in solvents of a broad spectrum of polarity. The compound (5) is well soluble in the solvents such as water, alcohols, ethers, esters and in aromatic and halogenated solvents (for comparison, the compound $CNCH_2CO_2K$ is well soluble only in very polar solvents such as water and alcohols). Thanks to good solubility, the compound (5) may be successfully employed for purification of various types of post-reaction mixtures.

The invention claimed is:

1. A method for removing one or more ruthenium-containing complexes, residues or compounds from a composition comprising one or more ruthenium-containing complexes, residues or compounds, the method including:
contacting the composition with a metal scavenger of formula (1) to provide a purification mixture,

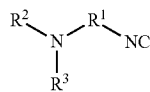

1 wherein, $R^1$ represents $C_2$-$C_{25}$ alkyl, $C_2$-$C_{25}$ alkenyl, $C_2$-$C_{25}$ alkynyl, $C_3$-$C_7$ cycloalkyl, $C_3$-$C_{25}$ cycloalkenyl, $C_8$-$C_{25}$ cycloalkynyl, $C_5$-$C_{24}$ aryl, $C_5$-$C_{20}$ heteroaryl or $C_3$-$C_{12}$ heterocyclyl, each being unsubstituted or substituted with at least one isonitrile (—NC) group; and
$R^2$ and $R^3$ represent, independently from each other, $C_2$-$C_{25}$ alkyl, $C_2$-$C_{25}$ alkylalkoxy, $C_1$-$C_{25}$ alkylamino, $C_2$-$C_{25}$ alkoxy, $C_2$-$C_{25}$ alkenyl, $C_3$-$C_7$ cycloalkyl, $C_3$-$C_{25}$ cycloalkenyl, $C_2$-$C_{25}$ alkynyl, $C_8$-$C_{25}$ cycloalkynyl, $C_5$-$C_{24}$ aryl, $C_5$-$C_{20}$ heteroaryl or $C_3$-$C_{12}$ heterocyclyl, or
$R^2$ and $R^3$ may be bound together to form a heterocyclic $C_4$-$C_{16}$ system, being unsubstituted or substituted with at least one or more isonitrile (—NC) group or (—R'NC) group, wherein R' represents $C_1$-$C_{12}$ alkyl, $C_5$-$C_{24}$ aryl, $C_5$-$C_{20}$ heteroaryl or $C_3$-$C_{12}$ heterocyclyl, being unsubstituted or substituted with at least one isonitrile (—NC) group.

2. The method of claim 1 wherein,
$R^1$ represents $C_2$-$C_{25}$ alkyl, $C_2$-$C_{25}$ alkenyl, $C_2$-$C_{25}$ alkynyl, $C_3$-$C_7$ cycloalkyl, $C_3$-$C_{25}$ cycloalkenyl, $C_8$-$C_{25}$ cycloalkynyl, $C_5$-$C_{24}$ aryl, $C_5$-$C_{20}$ heteroaryl or $C_3$-$C_{12}$ heterocyclyl; and
$R^2$ and $R^3$ represent, independently from each other, $C_2$-$C_{25}$ alkyl, $C_2$-$C_{25}$ alkylalkoxy, $C_1$-$C_{25}$ alkylamino, $C_2$-$C_{25}$ alkoxy, $C_2$-$C_{25}$ alkenyl, $C_3$-$C_7$ cycloalkyl, $C_3$-$C_{25}$ cycloalkenyl, $C_2$-$C_{25}$ alkynyl, $C_8$-$C_{25}$ cycloalkynyl, $C_5$-$C_{24}$ aryl, $C_5$-$C_{20}$ heteroaryl or $C_3$-$C_{12}$ heterocyclyl, being unsubstituted or substituted with at least one isonitrile (—NC) group, or
$R^2$ and $R^3$ may be bound together to form a heterocyclic $C_4$-$C_{16}$ system, being unsubstituted or substituted with isonitrile (—NC) group or (—R'NC) group, wherein R' represents $C_1$-$C_{12}$ alkyl.

3. The method of claim 1 wherein
$R^1$ represents $C_2$-$C_{25}$ alkyl, $C_2$-$C_{25}$ alkenyl, $C_2$-$C_{25}$ alkynyl, $C_3$-$C_7$ cycloalkyl, $C_3$-$C_{25}$ cycloalkenyl, $C_8$-$C_{25}$ cycloalkynyl, $C_5$-$C_{24}$ aryl, $C_5$-$C_{20}$ heteroaryl or $C_3$-$C_{12}$ heterocyclyl; and
$R^2$ and $R^3$ represent, independently from each other, $C_2$-$C_{25}$ alkyl, $C_2$-$C_{25}$ alkylalkoxy, $C_1$-$C_{25}$ alkylamino, $C_2$-$C_{25}$ alkoxy, $C_2$-$C_{25}$ alkenyl, $C_3$-$C_7$ cycloalkyl, $C_3$-$C_{25}$ cycloalkenyl, $C_2$-$C_{25}$ alkynyl, $C_8$-$C_{25}$ cycloalkynyl, $C_5$-$C_{24}$ aryl, $C_5$-$C_{20}$ heteroaryl or $C_3$-$C_{12}$ heterocyclyl, being unsubstituted or substituted with at least one isonitrile (—NC) group, or
$R^2$ and $R^3$ may be bound together to form a nitrogen-containing heterocycle selected from the group consisting of aziridine, azetidine, diazetidine, pyrrolidine, imidazolidine, oxazolidine, thiazolidine, piperidine, piperazine, morpholine, azepane, and 1,5,7-triaza-bicyclo[4.4.0]dec-5-ene, being unsubstituted or substituted with isonitrile (—NC) group or (—R'NC) group, wherein R' represents $C_1$-$C_{12}$ alkyl.

4. The method of claim 1 wherein,
$R^1$ represents $C_2$-$C_{25}$ alkyl, $C_3$-$C_7$ cycloalkyl, $C_5$-$C_{24}$ aryl, $C_5$-$C_{20}$ heteroaryl or $C_3$-$C_{12}$ heterocyclyl; and
$R^2$ and $R^3$ represent, independently from each other, $C_2$-$C_{25}$ alkyl, $C_2$-$C_{25}$ alkylalkoxy, $C_1$-$C_{25}$ alkylamino, $C_2$-$C_{25}$ alkoxy, $C_2$-$C_{25}$ alkenyl, $C_3$-$C_7$ cycloalkyl, $C_3$-$C_{25}$ cycloalkenyl, $C_2$-$C_{25}$ alkynyl, $C_8$-$C_{25}$ cycloalkynyl, $C_5$-$C_{24}$ aryl, $C_5$-$C_{20}$ heteroaryl or $C_3$-$C_{12}$ heterocyclyl, being unsubstituted or substituted with at least one isonitrile (—NC) group, or
$R^2$ and $R^3$ may be bound together to form a nitrogen-containing heterocycle selected from the group consisting of pyrrolidine, imidazolidine, oxazolidine, piperidine, piperazine, morpholine, azepane, and 1,5,7-triaza-bicyclo[4.4.0]dec-5-ene, being unsubstituted or substituted with isonitrile (—NC) group or (—R'NC) group, wherein R' represents $C_1$-$C_{12}$ alkyl.

5. The method of claim 1 wherein the composition is a post-reaction mixture of a reaction catalyzed with the one or more ruthenium-containing complexes, residues or compounds.

6. The method of claim 5 wherein the reaction is olefin-metathesis.

7. The method of claim 6 wherein the metal scavenger is of formulae (2), (3), (4) or (5):

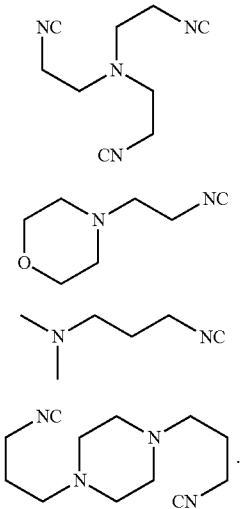

8. The method of claim 1 wherein the composition is a mixture of organic compounds contaminated with the one or more ruthenium-containing complexes, residues or compounds, wherein the organic compounds are products of an olefin-metathesis reaction.

9. The method of claim 1 wherein contacting the composition includes contacting the composition with two or more metal scavengers of formula (1).

10. The method of claim 1 wherein the composition further comprises an organic solvent, and the metal scavenger is dissolved in an organic solvent or water before contacting the composition.

11. The method of claim 1 wherein contacting the composition with the metal scavenger is carried out in a period from 1 minute to 48 hours.

12. The method of claim 1 wherein contacting the composition with the metal scavenger is carried out at a temperature ranging from 0 to 120° C.

13. The method of claim 1 further comprising filtering the purification mixture through a silica gel.

14. The method of claim 13 wherein the silica gel is in an amount of from 20 to 10000 weight % relative to the one or more ruthenium-containing complexes, residues or compounds.

15. The method of claim 1 further comprising:
combining silica gel with the purification mixture;
mixing the silica gel with the purification mixture; and
filtering off the silica gel.

16. The method of claim 15 wherein the silica gel is in an amount of from 20 to 10000 weight % relative to the one or more ruthenium-containing complexes, residues or compounds.

17. The method of claim 15 wherein mixing the silica gel with the purification mixture is carried out by stirring for a period from 1 minute to 48 hours.

* * * * *